United States Patent
Levine

(10) Patent No.: US 6,947,794 B1
(45) Date of Patent: Sep. 20, 2005

(54) SYSTEM AND METHOD WITH IMPROVED AUTOMATIC TESTING FUNCTIONS FOR DEFINING CAPTURE THRESHOLDS

(75) Inventor: Paul A. Levine, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 548 days.

(21) Appl. No.: 10/043,927

(22) Filed: Jan. 11, 2002

(51) Int. Cl.$^7$ .............................................. A61N 1/37
(52) U.S. Cl. ....................................................... 607/28
(58) Field of Search .............................. 607/11, 27, 28, 607/30, 29

(56) References Cited

U.S. PATENT DOCUMENTS

| | | | |
|---|---|---|---|
| 4,788,980 A | | 12/1988 | Mann et al. ........... 128/419 PG |
| 4,940,052 A | | 7/1990 | Mann et al. ........... 128/419 PG |
| 4,969,467 A | | 11/1990 | Callaghan et al. ..... 128/419 PG |
| 5,350,410 A | | 9/1994 | Kleks et al. .................... 607/28 |
| 5,411,533 A | | 5/1995 | Dubreuil et al. ............... 607/28 |
| 5,417,718 A | | 5/1995 | Kleks et al. .................... 607/28 |
| 5,458,623 A | * | 10/1995 | Lu et al. ......................... 607/28 |
| 5,601,615 A | * | 2/1997 | Markowitz et al. ............ 607/28 |
| 5,683,447 A | | 11/1997 | Bush et al. ................... 607/126 |
| 5,692,907 A | | 12/1997 | Glassel et al. ............... 434/262 |
| 5,713,933 A | * | 2/1998 | Condie et al. ................. 607/28 |
| 5,766,229 A | * | 6/1998 | Bornzin ......................... 607/28 |
| 5,855,594 A | | 1/1999 | Olive et al. .................... 607/28 |
| 5,861,012 A | | 1/1999 | Stroebel ........................ 607/28 |
| 5,991,656 A | | 11/1999 | Olson et al. .................... 607/4 |
| 6,021,351 A | | 2/2000 | Kadhiresan et al. .......... 607/19 |
| 6,044,298 A | | 3/2000 | Salo et al. ..................... 607/17 |
| 6,129,746 A | | 10/2000 | Levine et al. .................. 607/27 |

OTHER PUBLICATIONS

Levine, Paul A., M.D., "Clinical Experience with Dual Chamber Ventricular AutoCapture and Published in Cardiac Arrhythmias and Device Therapy: Results and Prospectives for the New Century", Ovsyshcher E (editor), Futura Publishing Co., Armonk NY, Chpt 42, pp: 339–348 (2000).

St. Jude Medical Bradycardia Devices Reference Manual, "AutoCapture™ Pacing System", Chapter 8, Copyrighted 2000.

Clarke, Malcolm, et al., "Automatic Adjustment of Pacemaker Stimulation Output Correlated with Continuously Monitored Capture Thresholds: A Multicenter Study", PACE, vol. 21, pp: 1567–1575 (Aug. 1998).

* cited by examiner

Primary Examiner—Jeffrey R. Jastrzab

(57) ABSTRACT

An implantable cardiac stimulation system capable of automatic capture verification is provided with an associated method for performing automatic testing functions using programmable, or automatically determined, AV delays. Automatic threshold testing and evoked response sensitivity testing performed at a user-specified AV delay setting, rather than a preset setting, allows assessment of automatic capture verification based on an AV delay relevant to daily system function. Further features of the present invention are an adjustable frequency with which automatic threshold tests are performed and an adjustable frequency with which threshold test results are stored in memory in a threshold record for better monitoring of lead stability or impending clinical problems. The frequency of performing threshold tests and the frequency of storing threshold test results may be varied according to the threshold stability. Stored threshold test results are advantageously displayed with respect to a fixed or variable time scale.

30 Claims, 7 Drawing Sheets

SYSTEM AND METHOD WITH IMPROVED AUTOMATIC TESTING FUNCTIONS FOR DEFINING CAPTURE THRESHOLDS

CROSS-REFERENCE TO RELATED APPLICATIONS

This application relates to copending U.S. patent application Ser. No. 10/043,718, filed Jan. 11, 2002, titled "System and Method with Improved Automatic Testing Functions for Automatic Capture Verification; and to copending U.S. patent application Ser. No. 09/952,902, filed Sep. 12, 2001, titled "Implantable Cardiac Stimulation System and Method for Measuring Atrioventricular Conduction and Adjusting Atrioventricular Hysteresis," both of which applications are assigned to the same assignee as the present invention, and are incorporated herein by reference.

FIELD OF THE INVENTION

The present invention is related to an implantable dual-chamber or multi-chamber cardiac stimulation device capable of performing automatic capture. More specifically, the present invention is directed to a cardiac simulation system and method for performing testing functions related to automatic capture using programmable test settings, such as AV delay, PV delay, and frequency of threshold test data recording.

BACKGROUND OF THE INVENTION

In the normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (A-V) node and a ventricular conduction system causing a depolarization known as an R-wave and the resulting ventricular chamber contractions.

Disruption of this natural pacemaking and conduction system as a result of aging or disease can be successfully treated by artificial cardiac pacing using implantable cardiac stimulation devices, including pacemakers and implantable defibrillators, which deliver rhythmic electrical pulses or anti-arrhythmia therapies to the heart at a desired energy and rate. A cardiac stimulation device is electrically coupled to the heart by one or more leads possessing one or more electrodes in contact with the heart muscle tissue (myocardium). One or more heart chambers may be electrically stimulated depending on the location and severity of the conduction disorder.

A stimulation pulse delivered to the myocardium must be of sufficient energy to depolarize the tissue, thereby causing a contraction, a condition commonly known as "capture." In early pacemakers, a fixed, high-energy pacing pulse was delivered to ensure capture. While this approach is straightforward, it quickly depletes battery energy and can result in patient discomfort due to extraneous stimulation of surrounding skeletal muscle tissue.

The capture "threshold" is defined as the lowest stimulation pulse output (as may be reported in terms of pulse duration, pulse amplitude, pulse energy, pulse current or current density) at which consistent capture occurs. By stimulating the heart chambers at or just above threshold, comfortable and effective cardiac stimulation is provided without unnecessary depletion of battery energy. Threshold, however, varies significantly from patient to patient due to variations in electrode systems used, electrode positioning, physiological and anatomical variations of the heart itself, and so on. Furthermore, threshold will vary over time within a patient as, for example, fibrotic encapsulation of the electrode occurs during the first few weeks after surgery. Fluctuations may even occur over the course of a day or with changes in medical therapy or disease state.

Hence, techniques for monitoring the cardiac activity following delivery of a stimulation pulse have been incorporated in modern pacemakers in order to verify that capture has occurred. If a loss of capture is detected by such "capture-verification" algorithms, the pacemaker output is automatically increased until capture is restored. A threshold test is then performed by the cardiac stimulation device in order to re-determine the threshold and automatically adjust the stimulating pulse output. While a primary parameter to vary for adjusting the stimulation pulse output is the voltage, it should be clear that other parameters could be adjusted as well, including pulse duration, energy, charge, and/or current density.

This approach, referred to as "automatic capture," improves the cardiac stimulation device performance in at least four ways: 1) by verifying that the stimulation pulse delivered to the patient's heart has been effective, 2) by maintaining the stimulation pulse output at the lowest level possible, thus 3) greatly increasing the device's battery longevity by conserving the energy used to generate stimulation pulses, yet 4) always protecting the patient by providing a significantly higher output back-up pulse in the setting of loss of capture associated with the primary pulse.

One implemented technique for verifying capture automatically by an implantable stimulation device involves monitoring the intra-cardiac electrogram signal, also referred to as EGM or IEGM, received on the cardiac stimulation and sensing electrodes. When a stimulation pulse is delivered to the heart, the EGM signals that are manifest concurrent with depolarization of the myocardium are examined. When capture occurs, an "evoked response" may be detected by special evoked response detection circuitry. The evoked response is the intracardiac atrial or ventricular depolarization that is observed as the P-wave or R-wave, respectively, on the surface ECG associated with a stimulus output. Detection of an evoked response indicates electrical activation of the respective cardiac tissue by the stimulating pulse. The depolarization of the heart tissue in response to the heart's natural pacemaking function is referred to as an "intrinsic response."

Through sampling and signal processing algorithms, the presence of an evoked response following a stimulation pulse is determined. A very short blanking period, or period of absolute refractoriness, following the stimulation pulse is applied to the evoked response sensing circuit immediately following the stimulation pulse to minimize or block out the stimulation pulse artifact.

This blanking period is followed by a special evoked response detection window, commonly 15 to 60 ms in duration, wherein the evoked response sensing circuit looks for an evoked response. For example, if a stimulation pulse is applied to the ventricle, an R-wave sensed by a special evoked response detection circuit of the pacemaker immediately following application of the ventricular stimulation pulse evidences capture of the ventricles.

If no evoked response is detected, a high-energy back-up stimulation pulse is delivered to the heart very shortly after the primary ineffective stimulus, typically within 60–100 ms of the primary pulse, in order to maintain the desired heart rate. If back-up stimulation pulses are required on two successive cycles, the system automatically begins to increase the stimulation output associated with the primary pulse until capture is restored, again for two consecutive cycles. Once capture is regained, an automatic threshold test is performed to re-determine the minimum pulse energy required to capture the heart at that time and adjust stimulation pulse output as needed.

An exemplary automatic threshold determination procedure is performed by progressively reducing the output from the functional output in 0.25 Volt steps until loss of capture occurs. With each loss of capture, a higher output back-up pulse is delivered in order to maintain the desired heart rate. Once loss of capture is achieved, the system increases the output in 0.125 Volt steps until stable capture is restored. Stable capture is defined as capture occurring on two consecutive primary pulses. Thus, reliable capture verification is of utmost importance in proper determination of the threshold.

Normally, capture threshold should be stable after the initial postoperative healing period. Frequent fluctuations in threshold can occur later, however, if a stimulating lead becomes dislodged, fractured, or its insulting sheath becomes discontinuous. Fluctuations in threshold may also reflect a change in clinical condition or the effects of a pharmacological agent. The automatic capture feature responds to such fluctuations by repeating a threshold test whenever the threshold rises enough to cause a loss of capture at the existing output setting. Threshold tests may also be repeated on a periodic basis to ascertain if a decrease in threshold has occurred. This automatic feature protects the patient by ensuring adequate stimulation pulse energy despite fluctuating threshold.

It is also desirable to store threshold test results on a frequent basis. Having a record of threshold changes over time will alert a medical practitioner to a possible lead failure or a change in the clinical condition of the patient, both of which warrant further medical evaluation. Such a feature is also referred to herein as "long term threshold record."

Sensing an evoked response during threshold tests or capture verification, however, can be difficult for several reasons. One confounding factor in accurate capture detection is "fusion." A fusion event occurs when a native depolarization and a stimulation pulse combine to contribute to the overall depolarization. The R-wave resulting from such a fusion event may be considerably diminished and not detectable by the normal R-wave detection scheme used for automatic capture verification. A fusion event may therefore easily be mistaken for a loss of capture.

Another somewhat related event that can confound accurate capture detection is "pseudofusion." Pseudofusion occurs when a stimulation pulse is delivered simultaneously with an intrinsic depolarization but in this case does not contribute at all to the overall depolarization. The resulting R-wave, however, is distorted as observed on the EGM resulting in a loss of capture detection when in fact a native R-wave has occurred.

In each of the above cases, the result may be a loss of capture detection by the cardiac stimulation device when in fact a native depolarization prevented the algorithm from recognizing that there was a successful cardiac depolarization. The loss of capture detection will cause the stimulation device to deliver a high-energy back-up stimulation pulse and invoke the threshold testing function in a chamber of the heart even though these actions are not clinically necessary.

To overcome the problem of fusion, and to prevent the intrinsic heart rhythm from interfering with the process of stimulation and capture during threshold testing, the time-out interval after which a stimulation pulse is delivered is commonly shortened in order to ensure stimulation occurs before a native depolarization. During single chamber stimulation, the escape interval is shortened; during dual chamber stimulation, the AV and PV delays are shortened. The AV delay is the interval following an atrial stimulation pulse that precedes delivery of a ventricular stimulation pulse. The PV delay is the interval following an atrial sensed P-wave preceding a ventricular stimulation pulse. By shortening the AV and PV delays, the ventricular pulse is delivered earlier than normally programmed following an atrial stimulation pulse or atrial sensed P-wave, respectively, and is expected to precede any natural depolarization of the ventricles.

However, in some patients, a shortened AV or PV delay can cause deleterious hemodynamic effects, which may contribute to adverse symptoms or hypotension. Furthermore, in patients with first degree or even more severe atrial-ventricular conduction block, the shortened AV and PV delays are not required in order to perform a threshold test without encountering fusion. Thus, automatic obligatory shortening of the AV and PV delays to a non-physiologic interval may be unnecessary and undesirable.

Another signal that interferes with the detection of an evoked response, and potentially the most difficult for which to compensate because it is usually present in varying degrees, is lead polarization. A lead-tissue interface is that point at which an electrode of the pacemaker lead contacts the cardiac tissue. Lead polarization is commonly caused by electrochemical reactions that occur at the lead-tissue interface due to application of an electrical stimulation pulse across the interface. If the evoked response is sensed through the same lead electrodes through which the stimulation pulses are delivered, the resulting polarization signal, also referred to as an "afterpotential", formed at the electrode can corrupt the evoked response signal that is sensed by the sensing circuits. This undesirable situation occurs often because the polarization signal can be three or more orders of magnitude greater than the evoked response. Furthermore, the lead polarization signal is not easily characterized; it is a complex function of the lead materials, lead geometry, tissue impedance, stimulation energy and other variables.

Before enabling the automatic capture function of a cardiac stimulation device, an automatic capture calibration algorithm is performed which includes an evoked response sensitivity test. During an evoked response sensitivity test, the amplitude of the sensed evoked response and the amplitude of the lead polarization signal are measured. The test is performed by delivering stimulation pulse pairs at a high output setting, typically 4.5 Volts. This high output setting provides a "worst case" scenario in terms of the lead polarization signal. The first stimulation pulse will capture the myocardium producing an evoked response signal. The second stimulation pulse is delivered shortly after the first pulse when the myocardium is physiologically refractory and capture is impossible. The second pulse will therefore produce only a lead polarization signal without an evoked response. The evoked response amplitude measured after the first pulse is then compared to the polarization signal amplitude measured after the second pulse.

The difference between these signals must meet a minimum requirement so that the automatic capture verification can reliably distinguish between an evoked response and pure polarization in order to appropriately recognize capture and loss of capture. Based on the difference between the evoked response signal and the polarization signal, the cardiac stimulation system can automatically recommend whether automatic capture should be enabled and, if so, provide a recommended evoked response sensitivity setting.

Just as during threshold testing the evoked response sensitivity test is typically performed at shortened AV and PV delays so that an accurate measurement of the evoked response amplitude may be made without interference from native R-waves. While this situation eliminates the problem of fusion for measurement purposes, it may not reflect the normal day-to-day operating conditions of the stimulation device. Automatic capture verification will be enabled with settings that are valid at the tested AV and PV delays but may not be the optimal settings at the final programmed AV and PV delay settings.

It would thus be desirable to provide an implantable dual-chamber or multi-chamber cardiac stimulation device possessing automatic capture in which threshold testing and evoked response sensitivity measurements are performed in a way that avoids the possibility of an adverse hemodynamic response in an individual patient and further provides realistic results regarding the day-to-day performance of the device. Further, it would be desirable to provide a threshold record capable of documenting fluctuations in threshold that occur over brief periods of time so that a clinician may better monitor lead stability or identify changes in clinical condition.

SUMMARY OF THE INVENTION

The present invention addresses these needs by providing a system and method for performing automatic threshold testing and evoked response sensitivity testing using programmable AV and PV delays in an implantable dual chamber or multichamber cardiac stimulation device. A further feature of the present invention is a programmable or variable frequency with which automatic threshold tests are performed, and a programmable or variable frequency with which threshold test results are stored in memory. Stored threshold test results are advantageously displayed graphically with respect to a fixed or variable time scale.

The system and methods of the present invention avoid obligatory shortening of the AV and PV delay settings, which may have undesirable effects in some patients, during automatic threshold testing and evoked response sensitivity testing. Providing programmable AV and PV delay settings during evoked response sensitivity testing further allows the clinician to better assess the actual behavior of the cardiac stimulation device based on its daily function.

By measuring the evoked response amplitude under conditions similar to the operating conditions selected for daily operation, a more accurate evoked response sensitivity setting may be determined, minimizing the likelihood of false loss of capture detections precipitating back-up stimulation and threshold testing. By allowing threshold test measurements and data storage to be performed according to clinician-programmed frequencies or variable frequencies, the clinician can better monitor lead stability or impending clinical problems revealed through atypical fluctuations in capture threshold. Intervals of time in which frequent threshold fluctuations were recorded may be displayed on an expanding time scale to allow more careful inspection.

The present invention provides an implantable cardiac stimulation system including: an implantable stimulation device capable of delivering therapeutic or test stimulation pulses to one or both atrial chambers of the heart and one or both ventricular chambers of the heart and capable of acquiring cardiac data; a set of leads for receiving atrial and ventricular signals and for delivering atrial and ventricular stimulation pulses; and an external programmer capable for performing desired testing functions, displaying received data, and communicating with the implantable device via a telemetry circuit to send or receive programmed operating parameters or cardiac data.

A preferred embodiment of the implantable stimulation device includes a control system for controlling the operation of the device, a set of sensing circuits comprised of sense amplifiers for sensing and amplifying the atrial and ventricular signals, and pulse generators for generating the atrial and ventricular stimulation pulses. In addition, the implantable device includes memory for storing operational parameters for the control system, such as AV and PV delay intervals and threshold testing and recording intervals. The implantable device also includes a telemetry circuit for communication with the external programmer.

The external programmer preferably includes: a user interface, such as a keyboard, mouse or touch screen; a control system for controlling the operation of functions or tests carried out by the external programmer; a memory for storing control programs, operational parameters, or data received from the implantable device; and a display apparatus such an LCD screen or printer. The external programmer also includes a telemetry unit for transmitting data to and from the implanted device.

In a preferred embodiment, the implanted stimulation device performs an evoked response sensitivity test by controlling the delivery of stimulation pulses by the implanted device and making the appropriate signal measurements. A telemetry wand placed over the implanted device allows for transmission of operating parameters and receipt of cardiac signal data. Ventricular stimulation pulses of sufficient energy to ensure ventricular capture are delivered at programmed AV and PV delays. The AV and PV delays may be advantageously selected to be equal to the AV and PV delay settings that will be selected for the day-to-day function of the implanted device. Based on the results of the evoked response sensitivity test, at the desired AV and PV delay settings, the clinician can make appropriate decisions in enabling the automatic capture feature and in selecting the evoked response sensitivity setting.

With automatic capture enabled, threshold testing will be invoked whenever loss of capture, defined as loss of capture on two consecutive primary pulses, occurs. In the preferred embodiment, the AV and PV delay settings during threshold testing are programmable by the user. In this way, the AV and PV delay settings can be tailored to individual patient need rather than automatically shortened to a required test setting. In patients whom experience negative hemodynamic affects during short AV or PV delay stimulation (25 to 50 msec) and who are not likely to experience frequent fusion or pseudofusion events, the clinician can select a more physiologic delay setting (e.g., 100 msec). For patients in whom the programmed AV and PV delays will result in consistent ventricular fusion, the evoked response signal amplitudes can be measured in the real-life situation to allow for identification and programming of the appropriate evoked response sensitivity value.

In a preferred embodiment, periodic threshold testing is also performed at a frequency that is programmable by the clinician, such as every one hour, two hours, four hours, etc. The results of threshold tests, whether performed according to a periodic trigger or due to a loss of capture, can be stored in memory in what is referred to herein as a "long term threshold record." The frequency by which threshold test results are written to memory is also preferably a programmable parameter. Furthermore, the frequency of threshold tests and/or the frequency of storing threshold test results may be automatically increased or decreased based on the instability or stability, respectively, of the measured threshold.

The implantable device is preferably capable of storing large amounts of data. Threshold data may be compressed as necessary to allow additional data to be stored. Stable threshold measurements may be overwritten by new data or compressed to a single data point with an appropriate time duration index. Preferably, abrupt changes in threshold, such as a change of more than 25% within 24 hours, are stored permanently in memory, with the corresponding date and time, until intentionally cleared from memory by a user. Stored threshold data may be downloaded to the external programmer at any time and displayed graphically for interpretation by a clinician. A variable, expanding time scale allows periods of fluctuating threshold to be examined more closely.

The system and method of the present invention thus improve the performance of dual chamber or multichamber cardiac stimulation systems possessing automatic capture by allowing greater flexibility in the operating parameters, specifically AV and PV delay, that control the threshold testing and evoked response sensitivity testing functions. AV and PV delay settings that are safe and appropriate for an individual patient may be selected by the user. Furthermore, evoked response sensitivity testing results will more accurately reflect the actual operating conditions of the implanted device. In addition, improved threshold measurement storage and display methods provided by the present invention provides the clinician valuable information in monitoring lead stability or other causes of threshold fluctuation.

BRIEF DESCRIPTION OF THE DRAWINGS

Further features and advantages of the present invention may be more readily understood by reference to the following description taken in conjunction with the accompanying drawings, in which.

DETAILED DESCRIPTION OF THE PREFERRED EMBODIMENTS

The following description is of a best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

The present invention is directed at improving the performance of the automatic capture feature in an implantable cardiac stimulation device possessing pacemaking, cardioversion and defibrillation capabilities. The performance of automatic capture is improved by providing programmable AV and PV delay settings during evoked response sensitivity testing and threshold testing. Furthermore, threshold test results may be stored in memory with a programmable or variable frequency of data collection to allow later display of fluctuations in capture threshold. An implantable cardiac stimulation device will thus be described in conjunction with FIGS. 1 and 2, in which the methods of the present invention could be implemented. It should be recognized, however, that numerous variations of such a device exist in which the methods of the present invention could be implemented without deviating from the scope of the present invention.

Figure 1:
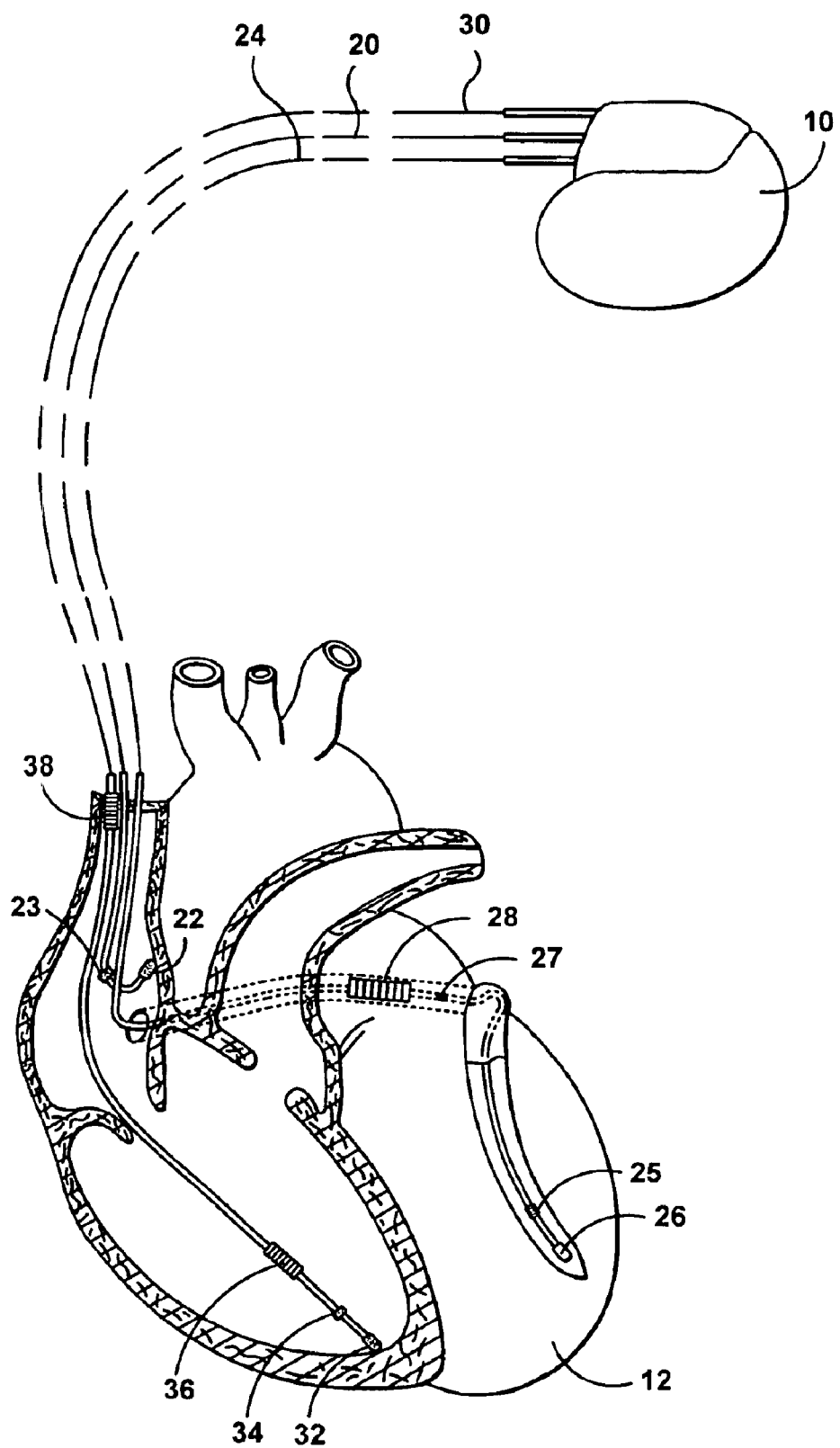
FIG. 1 is a simplified diagram illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense right atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. The right atrial lead 20 may also have a right atrial ring electrode 23 to allow bipolar stimulation or sensing in combination with the right atrial tip electrode 22.

To sense the left atrial and ventricular cardiac signals and to provide left-chamber stimulation therapy, the stimulation device 10 is coupled to a "coronary sinus" lead 24 designed for placement in the "coronary sinus region" via the coronary sinus ostium so as to place a distal electrode adjacent to the left ventricle and additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver: left ventricular pacing therapy using at least a left ventricular tip electrode 26, left atrial pacing therapy using at least a left atrial ring electrode 27, and shocking therapy using at least a left atrial coil electrode 28. In an alternative embodiment, the coronary sinus lead 24 may also include a left ventricular ring electrode 25.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
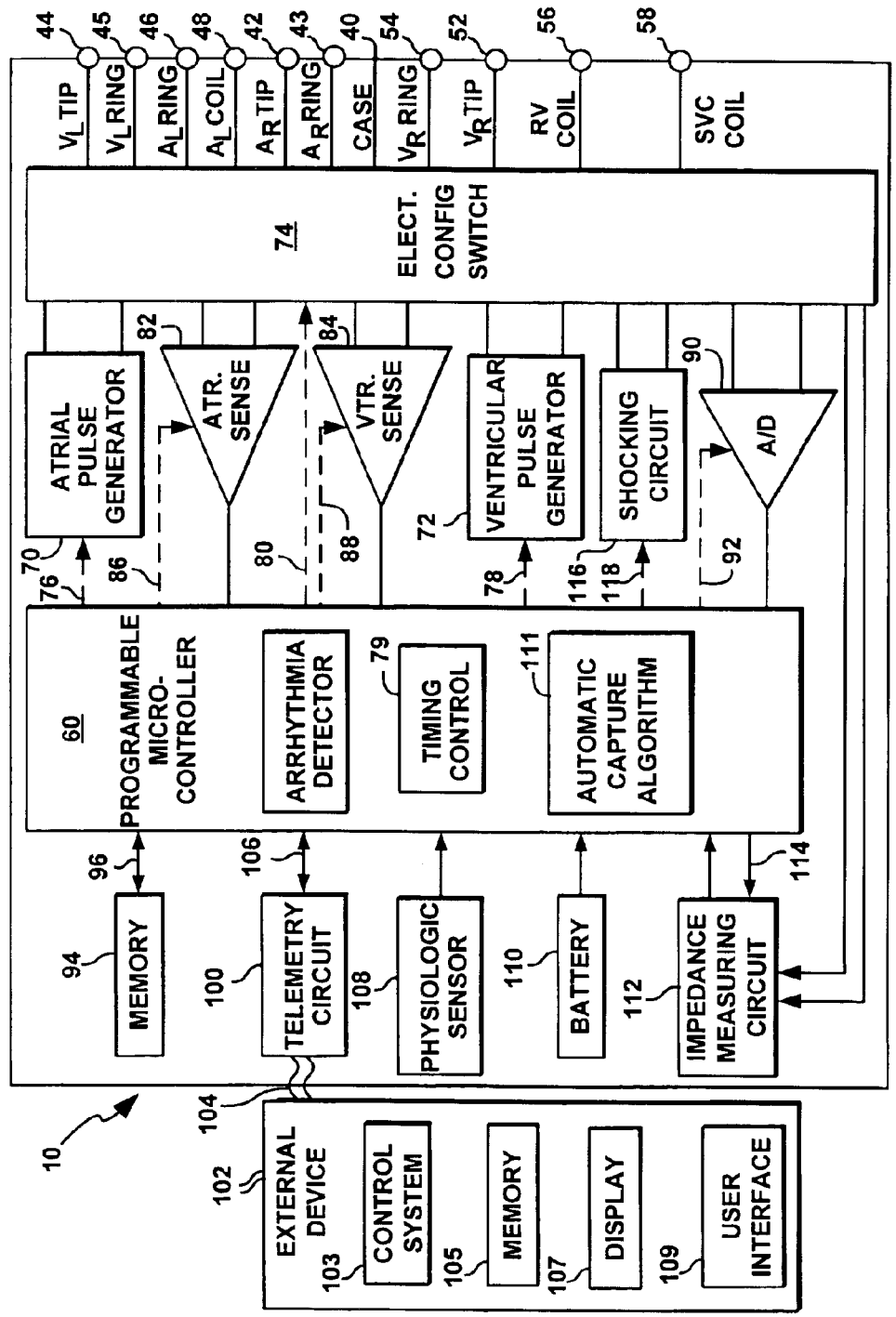
FIG. 2 is a functional block diagram of a multi-chamber implantable stimulation device illustrating the basic elements of a stimulation device that can provide cardioversion, defibrillation and pacing stimulation in four chambers of the heart.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The stimulation device 10 includes a housing 40 which is often referred to as "can", "case" or "case electrode", and which may be programmably selected to act as the return electrode for all "unipolar" modes. The housing 40 may further be used as a return electrode alone or in combination with one or more of the coil electrodes 28, 36, or 38, for shocking purposes. The stimulation device 10 further includes a connector having a plurality of terminals, 42, 44, 45, 46, 48, 52, 54, 56, and 58 (shown schematically and, for convenience, the names of the electrodes to which they are connected are shown next to the terminals). As such, to achieve right atrial sensing and stimulation, the connector includes at least a right atrial tip terminal 42 adapted for connection to the atrial (AR) tip electrode 22. The connector may also include a right atrial ring terminal (AR RING) 43 for connection to the atrial ring electrode 23, and a left ventricular ring (VL RING) 45 for connection to the left ventricular ring electrode 25.

To achieve left chamber sensing, pacing, and shocking, the connector includes at least a left ventricular tip terminal ($V_L$ TIP) 44, a left atrial ring terminal ($A_L$ RING) 46, and a left atrial shocking coil terminal ($A_L$ COIL) 48, which are adapted for connection to the left ventricular tip electrode 26, the left atrial ring electrode 27, and the left atrial coil electrode 28, respectively.

To support right ventricular sensing, pacing and shocking, the connector further includes a right ventricular tip terminal ($V_R$ TIP) 52, a right ventricular ring terminal ($V_R$ RING) 54, a right ventricular shocking coil terminal (RV COIL) 56, and an SVC shocking coil terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. The microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. Any suitable microcontroller 60 may be used that carries out the functions described herein.

FIG. 2 illustrates an atrial pulse generator 70 and a ventricular pulse generator 72 that generate stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g., pacing rate, atrial-ventricular (AV) delay, atrial interconduction (A—A) delay, or ventricular interconduction (V—V) delay, etc.), as well as to keep track of the timing of refractory periods, blanking intervals, noise detection windows, evoked response detection windows, alert intervals, marker channel timing, etc..

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, cross-chamber, etc.) by selectively closing the appropriate combination of switches.

Atrial sensing circuits (ATR. SENSE) 82 and ventricular sensing circuits (VTR. SENSE) 84 may also be selectively coupled to the right atrial lead 20, coronary sinus lead 24, and the right ventricular lead 30, through the switch 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch 74 determines the "sensing polarity" of the cardiac signal by selectively closing the appropriate switches. In this way, the clinician may program the sensing polarity independent of the stimulation polarity.

Stimulation during pacing can be performed in a bipolar mode in devices combining pacing and cardioversion/defibrillation functions because unipolar stimulation may interfere with arrhythmia detection. Hence, in one embodiment of the present invention, the switch bank 74 is configured such that: right atrial pacing and sensing is performed in a bipolar fashion between the right atrial tip electrode 22 and right atrial ring electrode 23; right ventricular pacing and sensing is performed in a bipolar fashion between right ventricular tip electrode 32 and right ventricular ring electrode 34; and left ventricular pacing and sensing is performed in a bipolar fashion between coronary sinus tip electrode 26 and the coronary sinus ring electrode 27. Right ventricular sensing may alternatively be configured between the right ventricular coil electrode 36 and the right ventricular ring electrode 34. Bipolar sensing may also be achieved using an integrated bipolar lead wherein the right ventricular coil electrode 36 and right ventricular ring electrode 34 are electrically coupled within the right ventricular lead body 30. Bipolar sensing is then performed between the right ventricular tip electrode 32 and the coupled right ventricular coil electrode 36 and right ventricular ring electrode 34. Any electrode combination that allows acceptable stimulation and sensing thresholds may be used. By employing the right ventricular coil electrode 36, possibly in combination with right ventricular ring electrode 34, the electrode surface during sensing is increased, advantageously reducing the effects of lead polarization. Other techniques of reducing lead polarization such as titanium nitride coating may also be used to improve the operation of the present invention.

Each sensing circuit, 82 and 84, preferably employs one or more low power, precision amplifiers with programmable gain and automatic gain or sensitivity control, bandpass filtering, and a threshold detection circuit, to selectively sense the cardiac signal of interest. The automatic sensitivity control enables the stimulation device 10 to deal effectively with the difficult problem of sensing the low amplitude signal characteristics of atrial or ventricular fibrillation.

The outputs of the atrial and ventricular sensing circuits, 82 and 84, are connected to the microcontroller 60 for triggering or inhibiting the atrial and ventricular pulse generators 70 and 72, respectively, in a demand fashion, in response to the absence or presence of cardiac activity in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry, and the timing of any blocking circuitry coupled to the inputs of the atrial and ventricular sensing circuits 82 and 84.

For arrhythmia detection, the stimulation device 10 includes an arrhythmia detector 77 that utilizes the atrial and ventricular sensing circuits 82 and 84 to sense cardiac signals, for determining whether a rhythm is physiologic or pathologic. As used herein "sensing" refers to the process of noting an electrical signal. "Detection" refers to the step of confirming that the sensed electrical signal as the signal being sought by the detector. As an example, "detection" applies to the detection of both proper rhythms (i.e., "R wave" or "R wave") as well as improper disrhythmias including arrhythmia and bradycardia (e.g., detection of the absence of a proper rhythm.)

The timing intervals between sensed events (e.g. P-waves, R-waves, and depolarization signals associated with fibrillation which are sometimes referred to as "F-waves" or "Fib-waves") are then classified by the arrhythmia detector 77 by comparing them to a predefined rate zone limit (e.g. bradycardia, normal, low rate ventricular tachycardia, high rate ventricular tachycardia, and fibrillation rate zones) and various other characteristics (e.g. sudden onset, stability, physiologic sensors, and morphology, etc.), in order to determine the type of remedial therapy that is needed (e.g. bradycardia pacing, anti-tachycardia stimulation, cardioversion shocks or defibrillation shocks, collectively referred to as "tiered therapy").

Cardiac signals are also applied to the inputs of a data acquisition system 90, which is depicted as an analog-to-digital (A/D) converter for simplicity of illustration. The data acquisition system 90 is configured to acquire intracardiac electrogram (EGM) signals, convert the raw analog data into digital signals, and store the digital signals for later processing and/or telemetry transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 may be coupled to the microcontroller 60 or another detection circuitry, for detecting an evoked response from the heart 12 in response to an applied stimulus, thereby aiding in the detection of "capture." The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, stimulation pulse amplitude, pulse duration, electrode polarity, rate, sensitivity, automatic features, arrhythmia detection criteria, and the amplitude, waveshape and vector of each stimulation pulse to be delivered to the patient's heart 12 within each respective tier of therapy. A feature of the present invention is the ability to sense and store a relatively large amount of data (e.g., from the data acquisition system 90), which data may then be used for subsequent analysis to guide the programming of the device. In a preferred embodiment, data resulting from periodic threshold tests are written to memory 94. The threshold measurement and the time and date at which it was made are stored in memory 94 so that changes in threshold over time may be graphically displayed on an external device 102, such as a programmer with an LCD display, after being downloaded via telemetry circuit 100 and communication link 104.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104. In a preferred embodiment, with a telemetry wand positioned over the stimulation device 10, an evoked response sensitivity test can be performed according to a control program located in external device 102, in this case a programmer. The methods of an evoked response sensitivity test in accordance with the present invention will be described in detail in conjunction with FIG. 3.

The stimulation device 10 may further include a physiologic sensor 108, commonly referred to as a "rate-responsive" sensor because it is typically used to adjust stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various stimulation parameters (such as rate, AV Delay, V—V Delay, etc.) at which the atrial and ventricular pulse generators 70 and 72 generate stimulation pulses.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time, preferably less than 10 µA, and also be capable of providing high-current pulses when the patient requires a shock pulse, preferably, in excess of 2 A, at voltages above 2 V, for periods of 10 seconds or more. The battery 110 preferably has a predictable discharge characteristic so that elective replacement time can be detected.

As further illustrated in FIG. 2, the stimulation device 10 is shown to include an impedance measuring circuit 112 that is enabled by the microcontroller 60 by means of a control signal 114.

In the case that it is a primary function of the stimulation device 10 to operate as an implantable cardioverter/defibrillator (ICD) device, it must detect the occurrence of an arrhythmia, and automatically apply an appropriate electrical stimulation or shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high (11 to 40 Joules) energy, as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38 (FIG. 1). As noted above, the housing 40 may act as an active electrode in combination with the RV coil electrode 36, or as part of a split electrical vector using the SVC coil electrode 38 or the left atrial coil electrode 28 (i.e., using the RV coil electrode 36 as a common electrode).

Cardioversion shocks are generally considered to be of low to moderate energy level (so as to minimize pain felt by the patient), and/or synchronized with an R-wave and pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
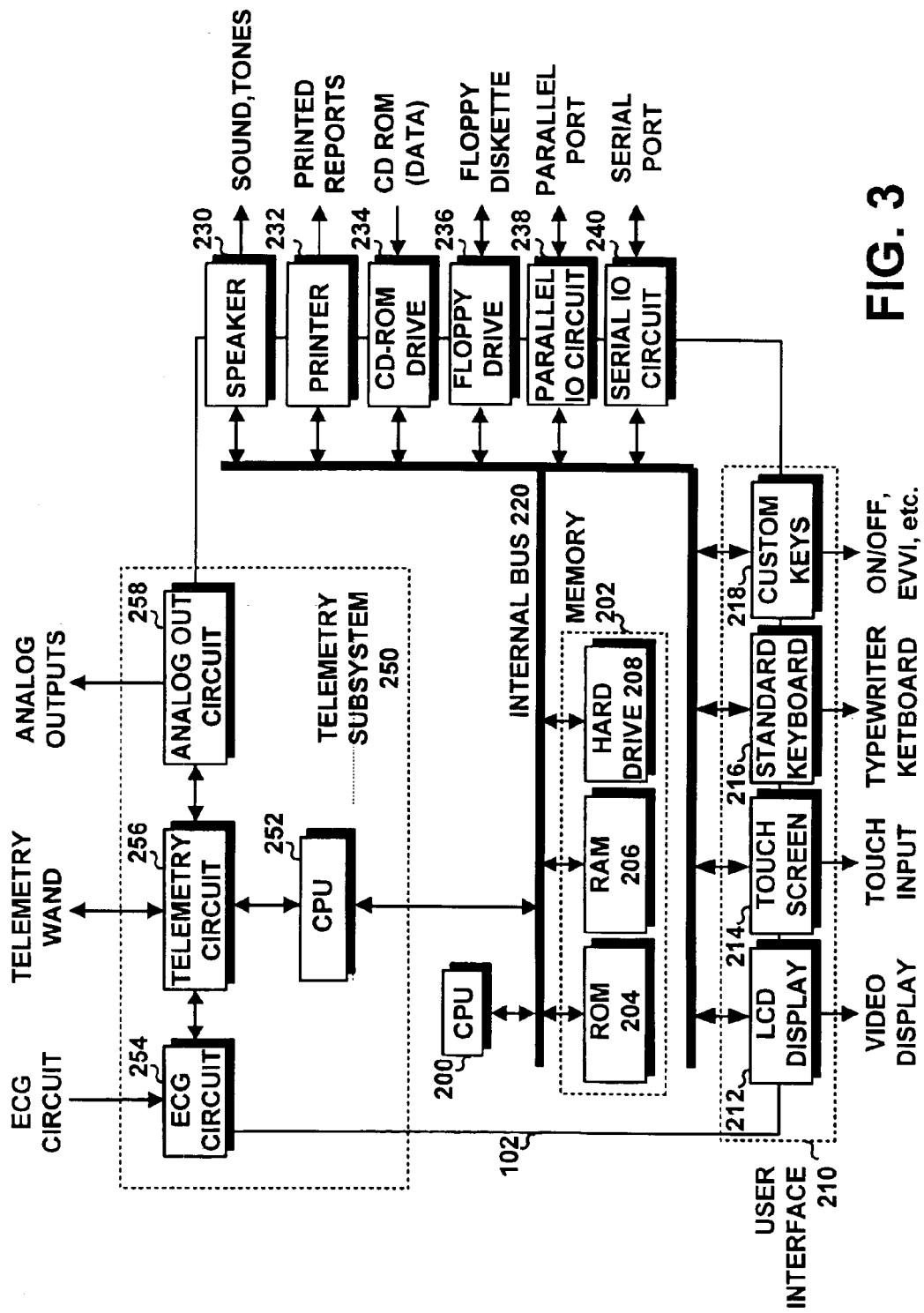
FIG. 3 is a block diagram illustrating the basic elements of an external device that can send and receive commands or data through telemetric communication with the implantable device of FIG. 2.

FIG. 3 illustrates a simplified block diagram of the external programming device 102 that communicates with device 10 through a telemetry circuit 100. The external device 102 includes a central processing unit (CPU) 200 that controls the operations carried out by the external device 102, such as programming the operating parameters of device 10 or carrying out various testing or diagnostic functions. Testing and diagnostic functions preferably include evoked response sensitivity testing, and may also include algorithms or methods for non-invasive programmed stimulation for arrhythmia induction, arrhythmia detection and termination testing, threshold testing, lead impedance measurements, etc.

CPU 200 is in communication with a memory (or data storage) 202 via an internal bus 220. The memory 202 may include a read-only memory (ROM) 204, a random access memory (RAM) 206, and hard drive 208. Operating parameters and algorithms controlling the programming and testing functions carried out by the external device 102 may be stored in memory 202 and accessed by CPU 200.

External device 102 is equipped with a user interface 210 that allows connection to an LCD display 212, a touch screen 214, a key board 216, and custom keys 218 that control a specific function or deliver a specific command automatically. Each component of the user interface 212 is also in communication with the CPU 200 and memory 202 via the internal bus 220 to allow user input, such as programming commands delivered using the touch screen 214, keyboard 216, or custom keys 218, to be received by the CPU 200 and/or stored in memory 202.

Programming selections made by a user and results of programming or testing operations may be displayed on the video display 212. Messages relating to the success of the programming command, recommended programmed settings, or warnings to the user regarding selected parameters may also be displayed on the video display 212.

The CPU 200 and memory 202 are also in communication with various input/output interfaces via the internal bus 220 that may include: a speaker 230 for delivering sounds or tones during the programming procedures; a printer 232 for printing results of programming or testing operations; a CD-ROM drive 234 and floppy drive 236 to which data from testing or programming operations may be written; and a parallel input/output port 238 and a serial input/output port 240 to allow connection to auxiliary equipment.

The external device 102 is further equipped with a telemetry subsystem 250. The telemetry subsystem 250 includes a central processing unit (CPU) 252 for controlling the transfer of data between the external device 102 and the implanted device 10. Thus, the telemetry CPU 252 is in communication with the internal bus 220 so that data may be transferred between the telemetry subsystem 250 the CPU 200, memory 202, user interface 210, and other input/output interfaces, 230, 232, 234, 236, 238, and 240.

The telemetry CPU 252 is connected to at least three interfaces which facilitate the receipt or transmission of data. An ECG circuit interface 254 allows connection to surface ECG leads for collecting a patient's ECG. The ECG may be displayed in real time on the video display 212. A telemetry circuit interface 256 allows connection to a telemetry wand that is placed over the implanted device 10 for receiving or sending data such as cardiac signal data stored in the memory 94 of device 10 or programmed operating parameters received at the user interface 210. An analog output circuit interface 258 allows connection to an analog output port to a remote printer or data recording system such as a hospital based electronic record.

Figure 4:
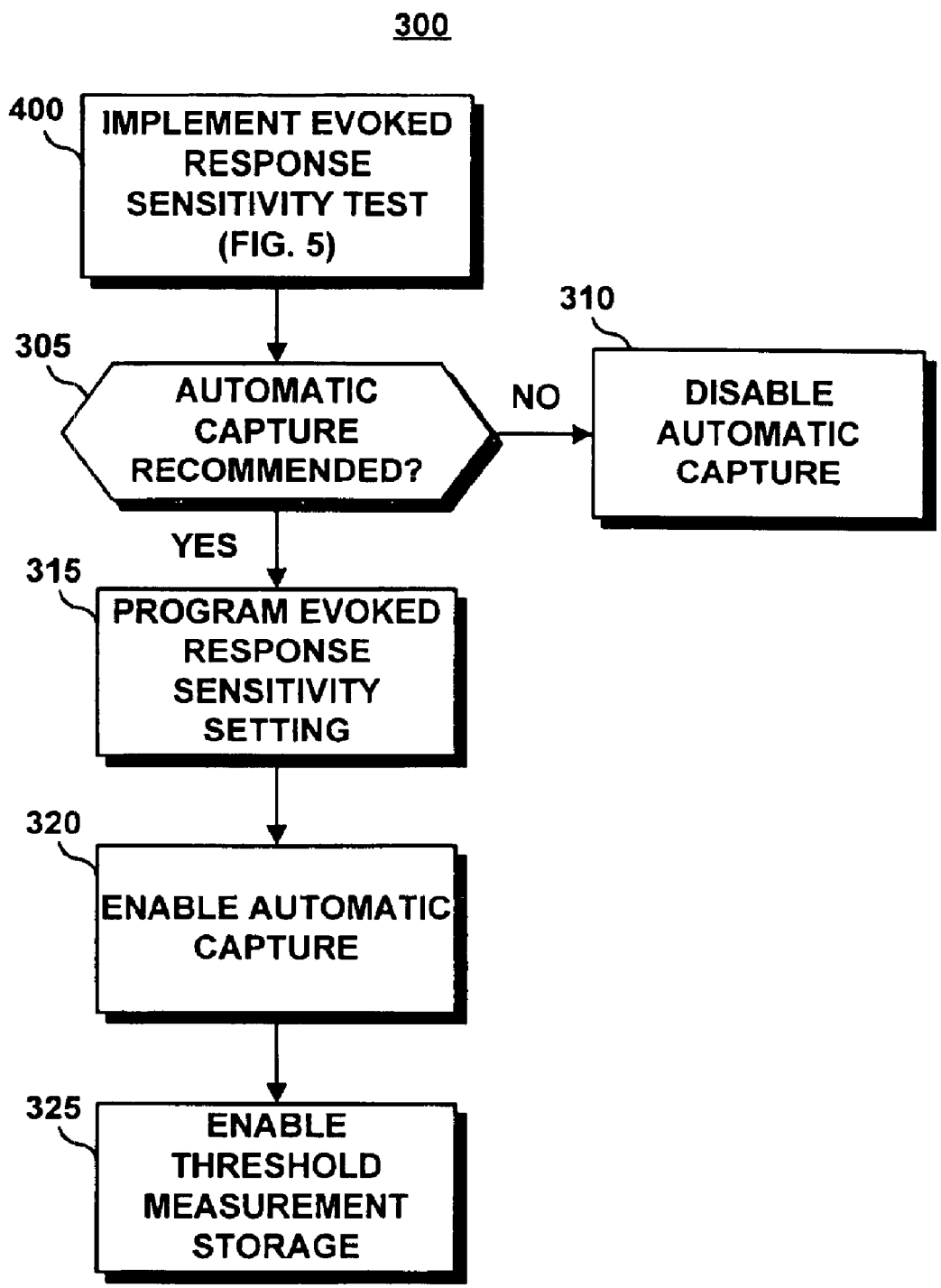
FIG. 4 is a process flow chart illustrating an overview of the operations included in the automatic capture feature of the implantable stimulation device of FIG. 2 and the external device of FIG. 3.

In FIG. 4, a flow chart is shown describing an overview of a process 300 implemented in one embodiment of the implanted device 10 and external device 102. In this flow chart, and the other flow charts described herein, the various algorithmic steps are summarized in individual "blocks". Such blocks describe specific actions or decisions that must be made or carried out as the algorithm proceeds. Where a microcontroller (a controller, or an equivalent device) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

At step 400 of FIG. 4, an evoked response sensitivity test is performed. This test is preferably executed by the external device 102 in communication with the implanted device 10. In an alternative embodiment, the algorithm for performing the evoked response sensitivity test 400 may be stored in the memory 94 of the implanted device 10 so that the implanted device 10 may perform the test 400. The details of the evoked response sensitivity test 400 will be described in conjunction with FIG. 5.

The results of the evoked response sensitivity test 400 will determine if enabling automatic capture is recommended. If automatic capture is not recommended, as determined at decision step 305, automatic capture is disabled automatically by a command transmitted from the external device 102 to the implanted device 10 at step 310. The user may subsequently choose to program automatic capture "on".

If automatic capture is recommended at decision step 305, a recommended evoked response sensitivity setting may be programmed by the user at step 315, and automatic capture may be programmed "on" (or enabled) at step 320. Automatic capture includes beat-by-beat capture verification and automatic threshold testing as will be described in greater detail in conjunction with FIG. 6.

At step 325, storage of threshold test measurements is also enabled. This action may occur automatically whenever automatic capture is enabled, or it may be programmable by the physician to be "on" or "off" independent of whether automatic capture is functioning. Details regarding the methods for storing threshold test results will be described in conjunction with FIGS. 5 and 6.

Figure 5:
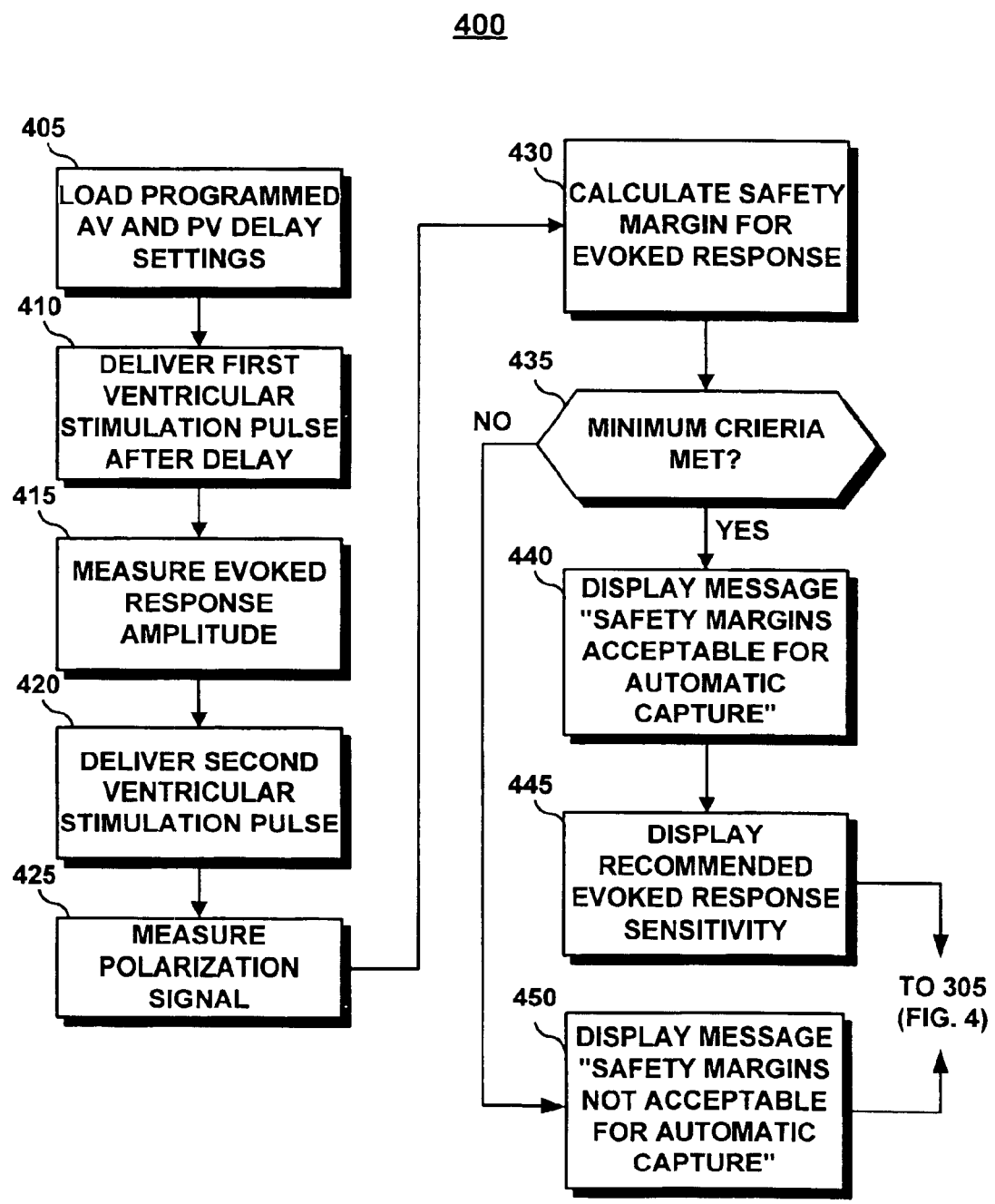
FIG. 5 is a process flow chart describing the method included in a preferred embodiment of the present invention for performing the evoked response sensitivity test included in the operations of FIG. 4.

The flow chart shown in FIG. 5 depicts the steps carried out during the evoked response sensitivity test 400 of FIG. 4. At step 405, the programmed AV and PV delay settings to be used during the evoked response sensitivity test are loaded. This step represents a novel feature of the evoked response sensitivity test of the present invention. Normally, the AV and PV delay settings are set automatically to short settings, typically 50 ms and 25 ms, respectively, in order to prevent fusion from interfering with the threshold measurement. However, according to one embodiment of the present invention, the user may program the AV and PV delay settings as deemed appropriate to a particular patient's need. For example, these settings may be equal to, or slightly shorter than the desired settings for day-to-day operation of device 10.

As an illustration, in a patient with complete heart block, the same AV or PV interval can be used for automatic capture, since there is no competition in a patient with some conduction. The AV or PV interval will be slightly shorter than the AV conduction delay to avoid fusion.

According to another embodiment, the AV and PV delay settings may be automatically set, as described in more detail in copending U.S. patent application Ser. No. 09/952,902, filed Sep. 12, 2001, titled "Implantable Cardiac Stimulation System and Method for Measuring Atrioventricular Conduction and Adjusting Atrioventricular Hysteresis."

During the evoked response sensitivity test 400, pairs of stimulation pulses will be delivered to the heart 12 at an amplitude and pulse width well above the capture threshold. Typically, a pulse amplitude of 4.5 V is used with a 0.4 ms pulse width. It should be clear that these values may be programmable.

At step 410, the first pulse is delivered after the programmed AV or PV delay following the next atrial stimulation pulse or sensed atrial P-wave, respectively. This first pulse will capture the ventricle so that the evoked response amplitude may be measured at step 415. The evoked response signal is sampled during an evoked response detection window, typically 15 to 60 ms in duration, beginning shortly after the stimulation pulse. The sampled signal is received by an automatic capture algorithm 111 (FIG. 2) that can be included in the A/D converter 90, as part of the ventricular sensing circuit 84, or as a separate component.

The second pulse of the pulse pair is delivered at step 420, typically 60 to 100 ms after the first pulse, so that it falls within the myocardial refractory period. During myocardial refractory, the myocardium cannot be depolarized, therefore the second stimulation pulse will not elicit an evoked response. However, the signal during the evoked response detection window is still sampled at step 425 following the second pulse in order to determine the amplitude of the lead polarization signal when no evoked response is present.

The evoked response and lead polarization signals are sampled for a desired number of pulse pairs, preferably a minimum of 10 pulse pairs. The evoked response sensing circuit has adjustable gain and sensitivity settings that are automatically adjusted during the evoked response sensitivity test.

In one embodiment, three gain settings are provided with a number of associated sensitivity levels. The gain settings are not programmable but are automatically adjusted by device 10. A set of pulse pairs, preferably five pulse pairs, are delivered at each gain setting. The evoked response signal and the lead polarization signal for each pulse pair is measured at the varying evoked response sensitivity settings.

These measurements allow the evoked response safety margin to be determined at step 430. The smallest evoked response signal (that is the worst case) is used to determine if the evoked response signal meets a set of minimum criteria required for automatic capture to be recommended. Preferably, the following four minimum criteria must be met:

1. the measured evoked response must be greater than 2.5 mV;
2. the measured lead polarization must be less than 4.0 mV;
3. the evoked response safety margin, defined as the ratio of the measured evoked response signal to the evoked response sensitivity value, must be $\geq 1.8:1$; and
4. the lead polarization safety margin, defined as the ratio of the evoked response sensitivity value to the measured lead polarization signal, must be $\geq 1.7:1$.

If the above conditions are met, as determined at decision step 435, a message indicating "the safety margins are acceptable for automatic capture" is displayed at step 440 on the LCD display 212. The recommended evoked response sensitivity value is then displayed at step 445. If the above criteria are not met, the message "the safety margins are not acceptable for automatic capture" is displayed at step 450 on the LCD display 212. The evoked response sensitivity test 400 is thus complete and the external programmer 102 returns to step 305 of FIG. 4 where it proceeds to prompt the user in programming automatic capture or will automatically disable automatic capture depending on the results of the test 400.

Figure 6:
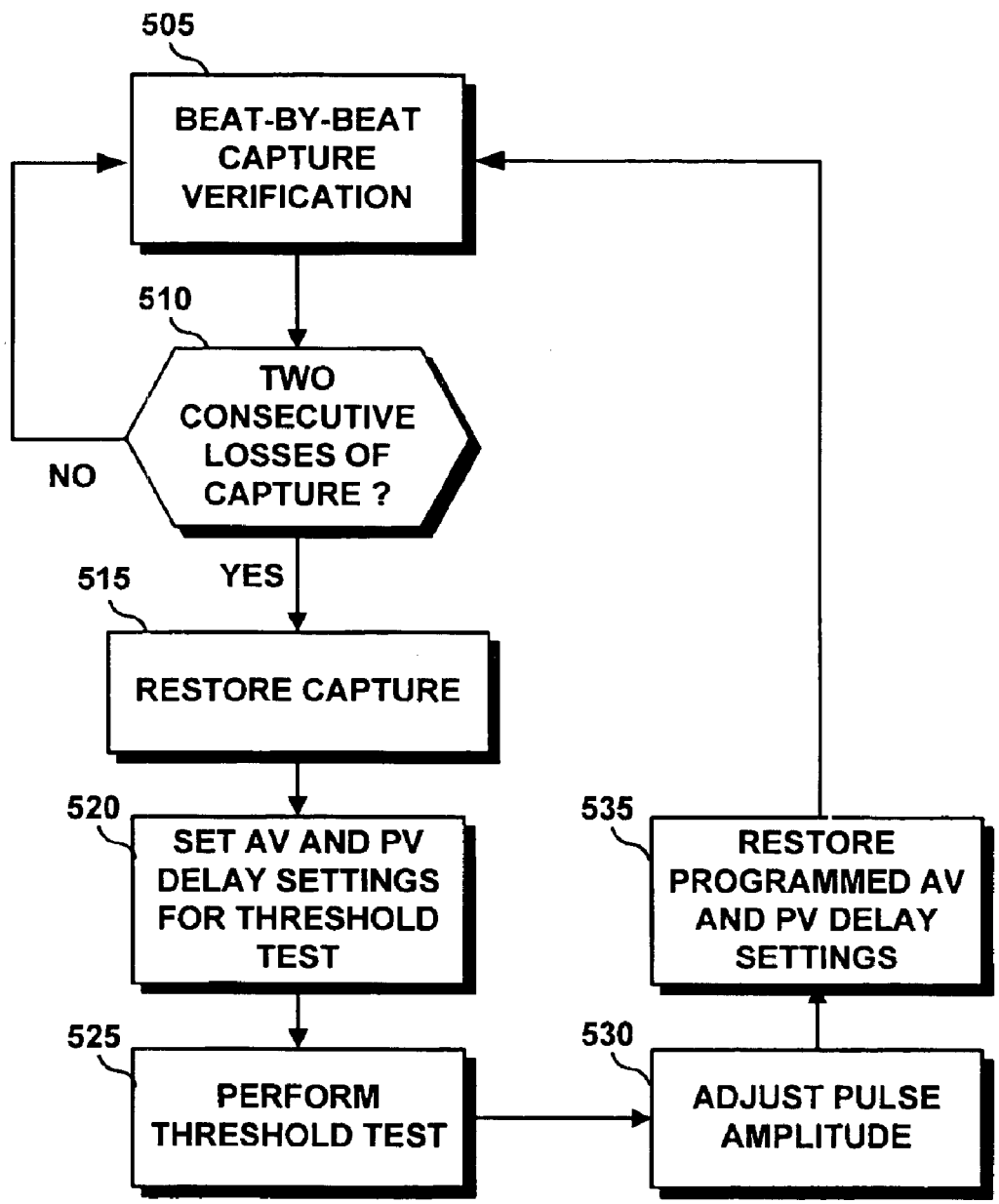
FIG. 6 is a process flow chart describing the methods included in a preferred embodiment of the present invention for performing automatic capture verification included in the operations of FIG. 4.

If automatic capture is enabled by the user at step 320 (FIG. 4), the automatic capture process 500 of FIG. 6 will be executed. Beginning at step 505, capture verification is performed preferably on a beat-by-beat basis, or alternatively on a less frequent, periodic basis. To verify capture, the ventricular signal is sampled during the evoked response detection window.

If the signal exceeds the programmed evoked response sensitivity setting, capture is verified. If the signal does not exceed the evoked response sensitivity setting, loss of capture is detected, and a back-up stimulation pulse is delivered shortly thereafter to maintain the desired heart rate. If two consecutive losses of capture occur, as determined at decision step 510, capture is restored automatically at step 515 by progressively increasing the programmed stimulation pulse amplitude or pulse width until capture is verified on two consecutive cycles.

Preferably, stimulation pulse amplitude is increased first by 0.25 Volt and thereafter by 0.125 Volt until capture is regained for two consecutive primary pulses. A back-up stimulation pulse is delivered whenever loss of capture is detected during this process.

Thereafter, a threshold test is performed at step 525 to re-determine the capture threshold. Before performing the threshold test, the AV and PV delay settings are set to the user-programmed settings for threshold testing at step 520. The AV and PV delay settings may alternatively be automatically set, as described in more detail in copending U.S. patent application Ser. No. 09/952,902, filed Sep. 12, 2001, titled "Implantable Cardiac Stimulation System and Method for Measuring Atrioventricular Conduction and Adjusting Atrioventricular Hysteresis," supra.

As stated earlier, typically, during a threshold test, the AV and PV delay settings are automatically shortened to 50 ms and 25 ms in order to prevent fusion from interfering with the threshold measurement. This automatic shortening may not be desirable in all patients, and thus the present invention provides a programmable AV and PV delay setting to be used during threshold testing. For example, these programmable settings may be equal to, or slightly shorter than the settings used for day-to-day operation of the device 10.

The threshold test performed at step 525 may be performed according to any algorithm that provides a reliable determination of capture threshold. Preferably, the threshold test is performed by progressively reducing the stimulation pulse amplitude from the existing, functional pulse amplitude in 0.25 Volt steps until loss of capture occurs. With each loss of capture, a higher output back-up pulse is delivered in order to maintain the desired heart rate. Once loss of capture is achieved, the output is increased in 0.125 Volt steps until stable capture, defined as capture occurring on two consecutive primary pulses, is restored. The setting at which stable capture first occurs is determined as the capture threshold.

After the capture threshold has been determined, the stimulation pulse amplitude is adjusted as needed at step 530. Preferably, the stimulation pulse amplitude is set equal to the capture threshold plus a working margin, commonly 0.25 Volts, to allow for small fluctuations in threshold. At step 535, the AV and PV delay settings are restored to the programmed values for normal device 10 operation, and the device 10 returns to step 505 to continue beat-by-beat capture verification.

Figure 7:
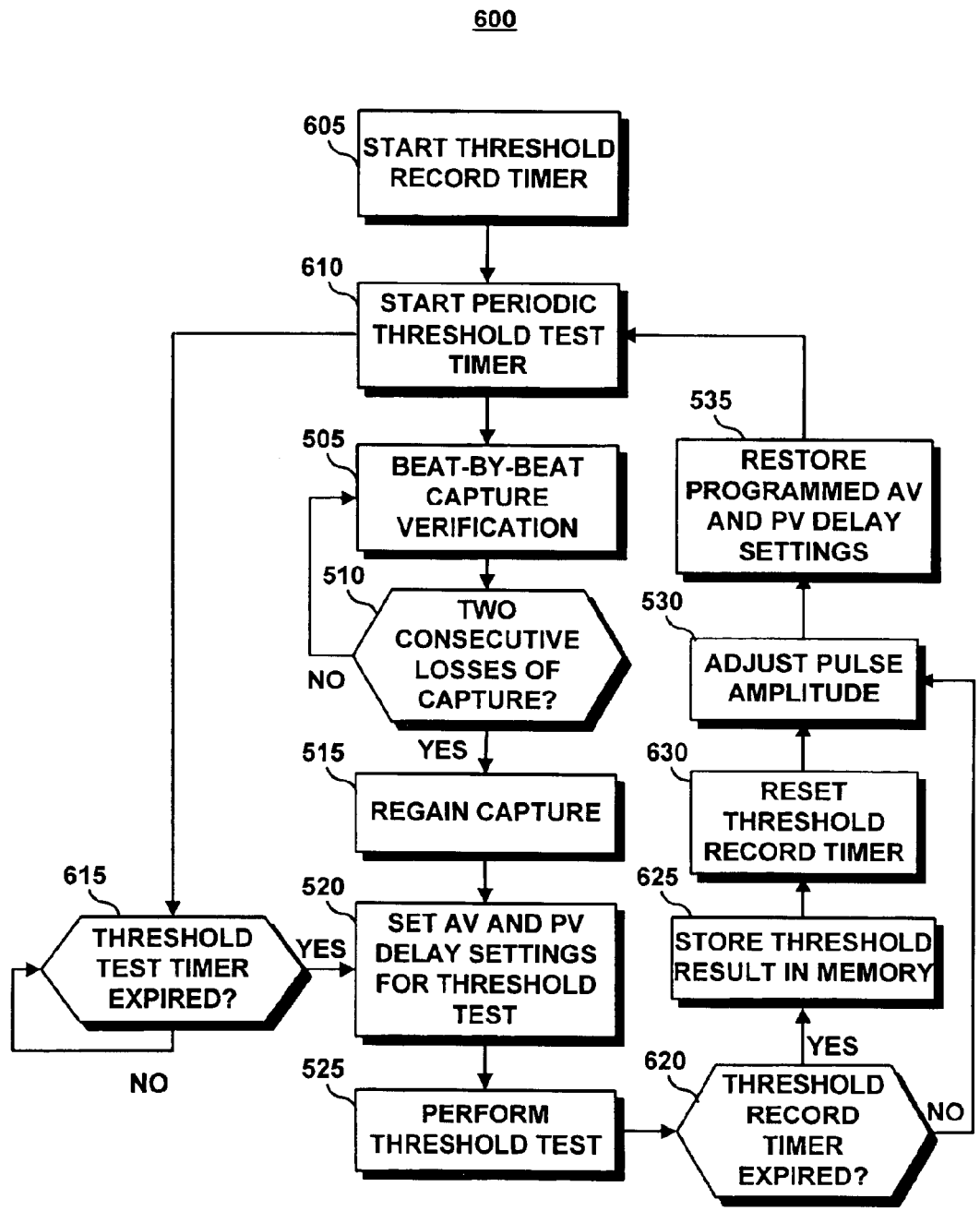
FIG. 7 is a process flow chart describing the methods included in a preferred embodiment of the present invention for storing threshold test results included in the operations of FIG. 4.

The flow diagram shown in FIG. 7 illustrates a process 600 for storing threshold test results if threshold measurement storage has been enabled (step 325, FIG. 4) as well as automatic capture. At step 605, a threshold record timer is started, which upon expiration indicates that the result of the next threshold test should be written to memory 94.

In one embodiment, the frequency for storing threshold test results, e.g., hourly, daily, etc., may be programmed by the user. In a preferred embodiment, recording threshold test results is performed with variable frequency according to the stability of the capture threshold measurements. If a large change in capture threshold is measured, the frequency of recording threshold tests is automatically increased. If capture threshold results are stable, the frequency of recording threshold test results is automatically reduced. For example, initially threshold test results may be recorded once daily. If a rise in threshold of 25% or more occurs within a 24-hour period of time, the frequency of recording the threshold test result will be increased, e.g., to every eight hours.

At step 610, another timer is started that determines the frequency of periodic threshold testing. Periodic threshold testing may be performed at the same frequency as threshold test result recording or it may be performed more often or less often. If performed more often, the result will only be stored in memory whenever the threshold record timer has expired. If performed less often, the result of the next threshold test performed in response to a loss of capture will be stored in memory upon expiration of the threshold record timer.

The frequency of periodic threshold testing is preferably programmable by the user. In the acute phase, periodic threshold tests may be programmed to occur more frequently, for example every eight hours. In the chronic phase, after electrode implantation has stabilized, periodic threshold tests may be programmed to occur less frequently, for example every 24 hours. In an alternative embodiment, the periodic threshold testing may also be performed on a variable basis depending on the stability of the threshold measurements. For a description of variable frequency threshold testing, see U.S. Pat. No. 6,129,746 to Levine et al., which is incorporated herein by reference in its entirety.

Some reference numerals used to describing process 600 of FIG. 7 are the same as those used to describe process 500 of FIG. 6 to indicate the same or similar steps. At step 505 of FIG. 7, automatic capture verification occurs on a beat-by-beat basis. Whenever two consecutive losses of capture occur (step 510), capture is regained at step 515 by progressively increasing the stimulation pulse amplitude. A threshold test will be performed at step 525 after setting the AV and PV delay settings to the programmed test settings at step 520. Alternatively, and as stated earlier, these delay settings can be set automatically by the stimulation device 10.

Whenever the periodic threshold test timer expires, as determined at decision step 615, the AV and PV delay settings will also be adjusted to the programmed threshold test settings at step 520 and a threshold test will be performed at step 525, regardless of whether a loss of capture has occurred. Such periodic threshold testing will allow detection of a decrease in capture threshold. An undetected decrease in capture threshold poses no risk to the patient, but battery energy is wasted since stimulation pulse amplitude could be reduced and still provide effective myocardial depolarization.

If the threshold record timer has expired at decision step 620, the threshold test result is stored in memory 94 at step 625, with the corresponding time and date. The threshold test result is stored regardless of whether the threshold test has been performed as a periodic test or as the result of a loss of capture. After storing the threshold test result, the threshold record timer is reset at step 630. The stimulation pulse amplitude is adjusted if necessary according to the threshold test result at step 530. The programmed AV and PV delay settings for day-to-day device 10 operation are restored at step 535.

If the threshold record timer has not expired at decision step 620, the threshold measurement in not stored in memory 94. Rather, the pulse amplitude is immediately adjusted at step 530, and the device 10 returns to beat-by-beat capture verification at the restored AV and PV delay settings.

The threshold data written to memory 94 at step 625 is preferably stored using compression algorithms that allow a variable amount of data to be collected. Consecutive threshold measurements of equal value are preferably compressed to a single data point with the corresponding time duration. Normally, the oldest data point is overwritten by the newest data point. However, data points that represent abrupt changes in threshold, e.g., more than 25% change in less than 24 hours, are stored permanently. These data points cannot be overwritten until they have been downloaded and cleared from memory 94 by the user.

The threshold results stored in memory 94 may be downloaded to the external device 102 upon delivery of a user command. The threshold results are then displayed with relation to time on LCD display 212. In the preferred embodiment, the time scale is variable. Thus, periods of time in which frequent threshold measurements were recorded due to large variability in the threshold can be viewed more carefully by expanding the time scale of a selected interval of time. Observations of fluctuations in capture threshold are useful to an attending clinician in identifying a problem with lead performance or a change in the patient's clinical state.

Thus, a dual-chamber or multi-chamber cardiac stimulation system and method have been described which allow evoked response sensitivity testing and threshold testing to be performed at programmable, or automatically determined AV and PV delays. Further, the system and method described allow threshold test measurements to be recorded in memory according to variable or programmable recording frequencies and later displayed graphically with respect to a variable time scale. These features improve the performance of an implantable stimulation device possessing automatic capture by allowing AV and PV delays for testing algorithms to be selected based on patient need.

The device performance is further improved by determining recommended automatic capture settings based on tests representative of the day-to-day function of the device. The device performance is further improved by allowing valuable threshold measurement data to be stored and displayed. Those skilled in the art may modify features or methods described herein without departing from the scope of the present invention.

What is claimed is:

1. A method of performing an automatic capture threshold test in an implantable cardiac stimulation device, the method comprising:
   loading an adjustable, user-provided atrio-ventricular delay setting;
   delivering a series of ventricular stimulation pulses following successive expirations of the atrio-ventricular delay setting;
   verifying if capture occurs for each ventricular stimulation pulse; and
   defining a ventricular capture threshold based on capture verification data.

2. The method of claim 1, wherein delivering the series of ventricular stimulation pulses comprises:
   delivering a first ventricular pulse following the expiration of a first atrio-ventricular delay setting; and
   delivering a second ventricular pulse following the expiration of a second user-provided atrio-ventricular delay setting, during a myocardial refractory period to avoid myocardium depolarization.

3. The method of claim 2, wherein loading the adjustable, user-provided atrio-ventricular delay setting comprises loading an AV delay setting.

4. The method of claim 2, wherein loading the adjustable, user-provided atrio-ventricular delay setting comprises loading a PV delay setting.

5. The method of claim 1, further comprising adjusting a frequency of performing a periodic threshold test based on capture threshold stability.

6. The method of claim 5, further comprising adjusting a frequency of storing the ventricular capture threshold based on the capture threshold stability.

7. The method of claim 5, wherein defining the ventricular capture threshold comprises storing a lowest stimulation output at which ventricular capture was verified.

8. The method of claim 1, further comprising storing the atrio-ventricular delay setting.

9. The method of claim 1, further comprising performing the threshold test in response to a loss of capture detection.

10. The method of claim 9, wherein performing the threshold test comprises performing the threshold test on a periodic basis.

11. The method of claim 1, further comprising storing a capture threshold in a threshold record.

12. The method of claim 11, wherein storing the capture threshold in the threshold record comprises adjustably storing the capture threshold on a periodic basis, based on the stability of the ventricular capture threshold.

13. The method of claim 11, wherein storing the capture threshold comprises storing a first capture threshold in a threshold record, which first capture threshold is not overwritten by a second capture threshold when the first capture threshold is determined to be unstable.

14. The method of claim 11, wherein storing the capture threshold comprises storing a first capture threshold in a threshold record, and overwriting the first capture threshold by a second capture threshold when the first capture threshold is determined to be stable.

15. The method of claim 11, further comprising storing a first capture threshold in a threshold record and compressing data from consecutively defined capture thresholds of equal value.

16. The method of claim 11, further comprising displaying the capture threshold stored in the threshold record.

17. The method of claim 16, further comprising monitoring lead stability using the threshold record.

18. The method of claim 16, further comprising monitoring a clinical condition of a patient using the threshold record.

19. A cardiac stimulation device comprising:
   a control circuit that loads an adjustable, user-provided atrio-ventricular delay setting to perform an automatic capture threshold test;
   a pulse generator coupled to the control circuit, that selectively generates stimulation pulses for delivery to at least one cardiac chamber;
   one or more electrodes, connected to the pulse generator, that deliver a series of ventricular stimulation pulses following successive expirations of the atrio-ventricular setting; and
   wherein the control circuit verifies if capture occurs for each ventricular stimulation pulse, and defines a ventricular capture threshold based on capture verification data.

20. The cardiac stimulation device of claim 19, wherein the series of ventricular stimulation pulses comprise:
   a first ventricular pulse following the expiration of a first atrio-ventricular delay setting; and
   a second ventricular pulse following the expiration of a second atrio-ventricular delay setting, during a myocardial refractory period to avoid myocardium depolarization.

21. The cardiac stimulation device of claim 19, further comprising a timing circuit that adjusts a frequency of performing a periodic threshold test based on capture threshold stability.

22. The cardiac stimulation device of claim 21, wherein the timing circuit further adjusts a frequency of storing ventricular capture threshold data based on the capture threshold stability.

23. The cardiac simulation device of claim 19, wherein the atrio-ventricular delay setting comprises an AV delay setting.

24. The cardiac stimulation device of claim 19, wherein the atrio-ventricular delay setting comprises a PV delay setting.

25. The cardiac stimulation device of claim 19, wherein the control circuit performs the threshold test in response to a loss of capture detection.

26. The cardiac stimulation device of claim 19, further comprising a data storage device that stores capture threshold records.

27. A cardiac stimulation device comprising:

means for acquiring an adjustable user-provided atrio-ventricular delay setting to perform an automatic capture threshold test;

means for delivering a series of ventricular stimulation pulses following successive expirations of the atrio-ventricular delay setting;

means for verifying if capture occurs for each ventricular stimulation pulse;

and means for defining a ventricular capture threshold based on capture verification data.

28. The cardiac stimulation device of claim 27, wherein the verifying means performs the threshold test in response to a loss of capture detection.

29. The cardiac stimulation device of claim 27, wherein the atrio-ventricular delay setting is any of a user-provided AV delay value, or an automatically adjustable AV delay setting.

30. The cardiac stimulation device of claim 27, wherein the atrio-ventricular setting is any of a user-provided PV delay value, or an automatically adjustable PV setting.

* * * * *